US009995405B2

(12) United States Patent
Duncan (10) Patent No.: US 9,995,405 B2
(45) Date of Patent: Jun. 12, 2018

(54) STOPCOCK WITH DETENTS (71) Applicant: David R. Duncan, Penryn, CA (US)

(72) Inventor: David R. Duncan, Penryn, CA (US)

( * ) Notice: Subject to any disclaimer, the term of this patent is extended or adjusted under 35 U.S.C. 154(b) by 0 days. days.

(21) Appl. No.: 15/259,387

(22) Filed: Sep. 8, 2016

(65) Prior Publication Data

US 2017/0067568 A1   Mar. 9, 2017

Related U.S. Application Data (60) Provisional application No. 62/215,273, filed on Sep. 8, 2015.

(51) Int. Cl.
| *F16K 11/085* | (2006.01) |
| *A61M 39/22* | (2006.01) |
| *F16K 31/60* | (2006.01) |
| *F16K 35/04* | (2006.01) |
| *F16K 37/00* | (2006.01) |
| *F16K 27/06* | (2006.01) |

(52) U.S. Cl.
CPC ......... *F16K 11/0853* (2013.01); *A61M 39/22* (2013.01); *F16K 27/065* (2013.01); *F16K 31/602* (2013.01); *F16K 35/04* (2013.01); *F16K 37/0008* (2013.01); *A61M 2039/229* (2013.01)

(58) Field of Classification Search
CPC .. F16K 11/0853; F16K 27/065; F16K 31/062; F16K 35/04; F16K 37/0008; A61M 39/22
See application file for complete search history.

(56) References Cited

U.S. PATENT DOCUMENTS

| 3,957,082 | A |   | 5/1976  | Fuson |  |
|-----------|---|---|---------|-------|--|
| 4,049,020 | A | * | 9/1977  | Neveux ............. | B60H 1/00842 137/625.11 |
| 4,197,876 | A | * | 4/1980  | Lobdell .............. | A61M 39/223 137/625.47 |
| 4,207,923 | A | * | 6/1980  | Giurtino ............. | A61M 39/223 137/625.47 |
| 4,413,805 | A | * | 11/1983 | Green ................. | F16K 11/0704 251/297 |
| 4,593,717 | A |   | 6/1986  | Levasseur |  |
| 5,375,625 | A | * | 12/1994 | Reynolds ............ | F15B 13/0402 137/625.66 |
| 5,832,959 | A |   | 11/1998 | Szymczakowski |  |

(Continued)

*Primary Examiner* — Mary McManmon
*Assistant Examiner* — Kevin Barss
(74) *Attorney, Agent, or Firm* — Heisler & Associates (57) ABSTRACT An insert is rotatable relative to a housing to transition the stopcock between different operational states with various different ports being open or closed. The insert includes a manifold shaft which resides within a hollow core of a hub of the housing. The openings are brought into and out of alignment with ports in the housing to cause the stopcock to transition between operational states with two or more of the ports being open or all of the ports being closed. The manifold shaft and hollow core include either detent slots or detent ribs thereon which coact together to cause the ribs to reside within the slots when the insert is rotated to one of the desired operational states, and for the ribs and slots to be out of alignment when outside of one of the desired operational states. The stopcock thus tends to snap into desired operational states.

10 Claims, 7 Drawing Sheets (56) References Cited

U.S. PATENT DOCUMENTS

| | | | | |
|---|---|---|---|---|
| 6,050,286 | A * | 4/2000 | Kruer | F16K 11/0853 137/119.03 |
| 6,123,094 | A * | 9/2000 | Breda | F16K 11/0853 137/270 |
| 6,196,266 | B1 * | 3/2001 | Breda | F16K 11/0853 137/454.6 |
| 7,344,204 | B2 * | 3/2008 | Cayer | B60T 15/60 303/123 |
| 7,849,877 | B2 * | 12/2010 | Tan | F16K 11/0853 137/625.46 |
| 8,584,701 | B2 | 11/2013 | Duncan | |
| 8,910,662 | B2 * | 12/2014 | Tan | F16K 11/0853 137/625.46 |
| 2010/0054447 | A1 * | 3/2010 | DeConcilis | H04Q 3/66 379/220.01 |
| 2010/0191106 | A1 | 7/2010 | Koyama | |
| 2014/0053931 | A1 * | 2/2014 | Whitaker | F16K 11/0853 137/625.17 |
| 2014/0076431 | A1 | 3/2014 | Duncan | |

* cited by examiner

STOPCOCK WITH DETENTS

CROSS-REFERENCE TO RELATED APPLICATIONS

This application claims benefit under Title 35, United States Code § 119(e) of U.S. Provisional Application No. 62/215,273 filed on Sep. 8, 2015.

FIELD OF THE INVENTION

The following invention relates to stopcocks for control of fluid flow between multiple ports. More particularly, this invention relates to stopcocks such as medical stopcocks for control of medical liquids arriving from at least one source and leading to at least one output, which stopcocks are manually grippable and rotatable to control flow from a desired input to a desired output or to shut off flow altogether. More particularly, this invention relates to stopcocks which include structures to provide high reliability that the stopcock operational position selected by a user will actually be implemented in the physical arrangement of flow pathways through the stopcock, such as by providing detents which encourage the stopcock to only reside in certain relative orientations which correspond with predefined desirable operational states.

BACKGROUND OF THE INVENTION

Stopcocks are used in a variety of fluid flow handling systems as a convenient valve for opening or closing fluid conduits and selecting between multiple fluid conduits as to which fluid conduits are open and which fluid conduits are closed. One application for such stopcocks is in the medical field where patients have medicaments infused thereinto from various different sources and medical tubing supplying various different fluids and other medicament sources are routed to stopcocks at strategic locations for medical personnel to select fluid flow from various sources to various destinations.

Two such stopcocks are described in detail in U.S. Pat. No. 8,584,701 and U.S. Published Patent Application No. 2015/0129061, both incorporated herein by reference in their entireties. Such stopcocks generally include two parts which rotate relative to each other including a housing and an insert. The housing has a plurality of ports at a periphery thereof which can each be connected to medical tubing or some other fluid vessel. The ports lead to a central hub within the housing. The insert is coupled to the housing in a manner which allows the insert to rotate relative to the housing. The insert includes a manifold shaft which fits within a hollow core of the hub.

The manifold shaft has flow pathways therein which terminate at openings in the surface of the manifold shaft. When the insert is rotated to appropriate positions, the openings on the surface of the manifold shaft become aligned or misaligned with various different ports of the hub of the housing, so that fluid flow is allowed or impeded, depending on the orientation of the insert relative to the housing. Typically, a knob is provided on the insert to assist in rotating the insert. In some embodiments, indicator plates are provided which can be selectively alignable along with the openings in the manifold shaft relative to the ports, so that the indicator plate provides a visual indication as to which ports of the stopcock are open and which ports of the stopcock are closed.

It is important that a user have high confidence that the stopcock is properly oriented, such as to avoid medication errors when the stopcock is used in a medical environment. The potential exists for a user to not exactly align the ports of the housing with the openings in the manifold shaft, with such misalignment providing the potential for improper operation of the stopcock or leakage of the stopcock. Furthermore, there is the potential even when the stopcock has been appropriately positioned, for the stopcock to be inadvertently bumped out of a proper position into an improper position. Often medical practitioners that use stopcocks purposefully attempt to position the stopcocks into a malaligned configuration with the knob between ports (or otherwise malaligned) and presumes that all of the ports are closed ("off"). However, if the malalignment is not set exactly right there is risk that small amounts of medication will flow through the stopcock unrecognized. This can lead to medication errors or unwanted medication administration.

Accordingly, a need exists for stopcocks which can hold a proper position once properly selected and which encourage the stopcock towards discrete positions which are appropriate for allowing or preventing flow therethrough, rather than allowing any random position of the insert relative to the housing. A need also exists for stopcocks which can prevent leakage while still providing confidence that the stopcock is initially in its proper selected position and that it will maintain that proper position even if jostled or bumped. A need also exists for a stopcock that allows definitive positioning between the insert and the housing thereof, such that in at least one position none of the ports communicate and all of the ports are closed ("off").

SUMMARY OF THE INVENTION

With this invention, a stopcock is provided which includes detents to cause a rotating insert portion of the stopcock to snap into various discreet positions relative to the housing of the stopcock. Such discrete positions can be clearly recognizable by a medical professional as having a particular stopcock flow condition. The stopcock is also able to maintain a selected position unless significant forces are provided to cause the insert to be rotated to a new position.

In one embodiment and to implement such a stopcock with detents therein, the stopcock is configured as essentially a two-piece structure including a housing and an insert. The housing and insert fit together by translation of a manifold shaft of the insert into a hollow center of a hub of the housing. The manifold shaft of the insert is oriented coaxially with the hollow center of the hub, and along a central axis thereof.

The insert includes the manifold shaft with appropriate openings in a surface of the manifold shaft which communicate with manifold flow lines therein. One common form of valve has three ports within the housing, such as that depicted in the included figures. An insert for such a stopcock assembly would typically have a set of manifold paths which similarly have three openings which are oriented in a manner similar to the orientation of the ports within the housing. For instance, one might consider the openings to be at the 12 o'clock position, 3 o'clock position and 6 o'clock position passing through the manifold shaft, each of these manifold lines oriented within a common plane which is coplanar with the plane in which the three ports of the housing are located, when the insert has been fully inserted into the housing. With such a common orientation, multiple different flow conditions can be provided by rotation of the insert about the central axis.

One flow condition allows for each of the openings to be aligned with one of the ports so that each of the ports of the housing are simultaneously opened. In various other positions, any two of the three ports can be open while the other port is closed. In various other positions, all of the ports can be closed. In particular and with regard to the closed positions, the openings in the ends of the manifold lines are small enough relative to space between the ports and the hub of the housing so that when the ports are misaligned with the openings (such as by a 45° divergence relative to the openings in the manifold shaft), all of the openings of the manifold lines in the manifold shaft are closed so that all of the ports are closed.

Depending on the size of the openings in the manifold shaft and the size of fluid pathways extending from the ports to the hub, a slight misalignment away from this 45° in-between position which causes all of the ports to be closed, can fail and result in a small amount of leakage, rather than fully shutting off the stopcock. To avoid a stopcock which can be difficult to precisely orient where desired, a lower end of the hub is fitted with a plurality of detent prominences, such as ribs extending inwardly toward the central axis away from a cylindrical inner surface of the hub. These detent ribs preferably extend parallel to the central axis and have a constant size and shape which is generally semi-cylindrical. A tip of the manifold shaft of the insert is provided with a series of detent recesses, such as slots extending radially inwardly into the tip of the manifold shaft and toward the central axis. These detent slots have a semi-cylindrical shape and size which is selected to substantially match the shape and size and orientation of the detent ribs in the housing. The ribs and slots could be reversed so that the ribs are on the manifold shaft and the slots are on the hub inner surface.

By providing eight detent ribs and eight detent slots, and equally spacing them from each other (e.g. 45° apart), the detent slots and detent ribs can be precisely aligned at eight different radial orientations between the insert and the housing, circumferentially spaced from each other. The detent ribs and slots remain aligned with each other at each of these positions of the insert relative to the housing.

Furthermore, the detent ribs and slots are preferably positioned so that a detent rib is aligned with each of the ports and a detent slot is aligned with each of the openings in the manifold lines within the manifold shaft. As an alternative, the detent ribs and detent slots could each be a similar amount of misalignment from the ports and openings and still function according to this invention.

The height of the detent ribs and the height of the detent slots are selected so that when the insert is rotated relative to the housing and the detent slots come off of the detent ribs, a slight interference fit exists between the detent ribs and plateau portions of the tip of the insert between the detent slots. Hence, friction is present and the insert, while still rotatable, experiences some resistance. When the insert continues to be rotated until the slots come back into alignment with the ribs, the insert will tend to "snap" into this proper position which will either cause some of the ports to be precisely aligned with some of the manifold lines within the manifold shaft, or for all of the manifold lines to be fully out of alignment with the ports.

Keeping a medical stopcock from leaking can be a difficult task. One technique for avoiding stopcock leakage is to provide the size of the manifold shaft of the insert precisely matching a diameter of the hollow interior of the hub. Such precise sizing can be an exact match of sizes or can conceivably involve the manifold shaft of the insert having a slightly greater size than an interior diameter of the hollow core of the hub. In such a manner a very slight friction fit is provided between the manifold shaft and the hollow core of the hub. In either event, through careful control of tolerances during manufacturing, it is known to be able to keep a medical stopcock from leaking, and without requiring extensive and elaborate seals around each of the openings of the manifold lines and/or at fluid conduits extending inward from the ports of the housing.

Furthermore, by forming the insert and the housing from the same materials or materials with closely matched thermal expansion characteristics, such sealing and leakage avoidance can be further enhanced. Also, some plastic materials are to some degree hydrophilic and resist wicking of fluid through cracks therein, but instead have a tendency to resist fluid flow through microscopic gaps between interfacing surfaces. Through a combination of these techniques as well as others, it is known to manufacture medical stopcocks which substantially avoid leakage without requiring the elaborate seals described above. However, when adding detents to the stopcock, some strain and distortion is caused to occur in the portions of the stopcock adjacent to the detents, in that the ribs of the detent come into conflict with the plateaus between the slots in the detent, which strain loads cause sufficient distortion to surfaces of the stopcock that leakage potential is significantly enhanced.

Importantly with one embodiment of this invention, by providing a similar number of detent ribs and detent slots, sizing them similarly and spacing them radially in a similar pattern, the strain encountered by having detent ribs coming into conflict with spaces between detent slots is a highly uniform strain which is experienced radially uniformly near the tip of the manifold shaft. Furthermore, by preferably locating the detent ribs on the tip of the manifold shaft and elongating the manifold shaft slightly so that this distorting strain on the manifold shaft and hub is located a significant distance from the openings into the manifold lines and the fluid conduits extending to the ports, the distorting strain associated with the detents is isolated sufficiently that leakage is substantially prevented. Also, when snapped to a proper orientation, this strain subsides as the ribs each fit into a slot.

Furthermore, it is optional but desirable to have a seal trough and seal groove formed within the manifold shaft and the interior surface of the hollow hub at similar locations thereon. These seal troughs and seal grooves can receive an O-ring or seal of other shape therein which can be resilient in form and prevent leakage out of a lower portion of the stopcock. As an alternative to an O-ring, a bearing can be provided in this seal trough and seal groove area which is molded in place on the insert or housing and acts as an O-ring type seal, but does not require the additional assembly of placing a separate O-ring. The tip of the manifold shaft is typically closed, but could provide an opening for an axial flow option.

OBJECTS OF THE INVENTION

Accordingly, a primary object of the present invention is to provide stopcocks for control of fluid flow between at least one input and at least one output and which provide reliable holding of the stopcock in desired operational states and resists positioning of the stopcock in undesirable operational states.

Another object of the present invention is to provide a stopcock which avoids leaking, especially when an insert thereof is rotationally misaligned with the housing thereof.

Another object of the present invention is to provide a stopcock which tends to snap into either a desired open position or into a desired closed position.

Another object of the present invention is to provide a medical stopcock for control of flow of medical liquids in a highly reliable manner to avoid medication errors.

Another object of the present invention is to provide a medical stopcock which avoids leakage of potentially valuable medical liquids.

Another object of the present invention is to provide a medical stopcock which resists rotation of an insert relative to a housing to a position which is anything other than a clearly open position with a desired path through the stopcock or a clearly closed position, and resists positioning in orientations which are ambiguous.

Another object of the present invention is to provide a stopcock which clearly delineates the orientation and operational state that the stopcock is in and also is securely held in the indicated operational state.

Another object of the present invention is to provide a stopcock which resists a change in orientation thereof due to incidental contact or movement, for reliable operation thereof.

Other further objects of the present invention will become apparent from a careful reading of the included drawing figures, the claims and detailed description of the invention.

DESCRIPTION OF THE PREFERRED EMBODIMENT

Referring to the drawings, wherein like reference numerals represent like parts throughout the various drawing figures, reference numeral 10 is directed to a stopcock (FIG. 3) which has an insert 20 rotatable relative to a housing 70 to open or close flow through various ports 80 (by rotation along arrow B). The stopcock 10 is particularly configured with detents (such as detent slots 60 and detent ribs 100) to cause the stopcock 10 to be biased toward orientation only in particular operational states defining which ones of the ports are open or with all the ports closed, so that the stopcock 10 resists operation in an ambiguous and undesirable manner and encourages operation in a manner consistent with the orientation and operational state desired by the user of the stopcock 10.

Figure 1:
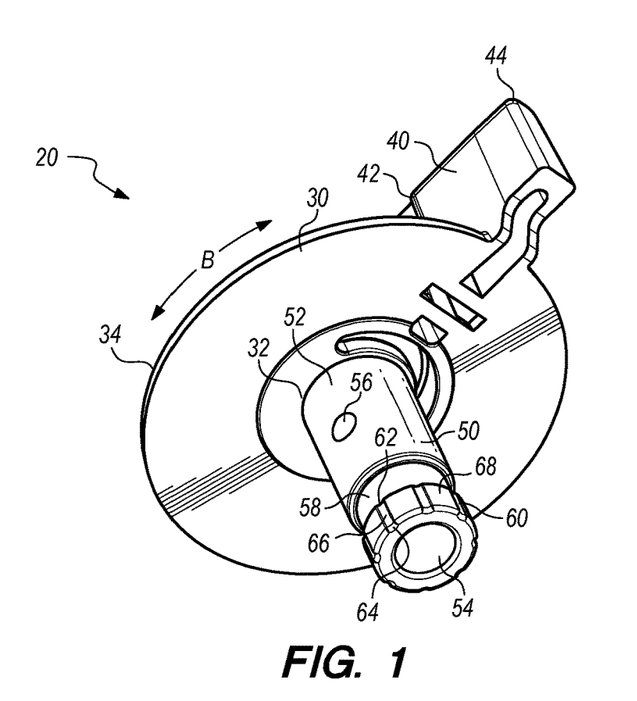
FIG. 1 is a perspective view of an insert of the stopcock of this invention according to a preferred embodiment.
Figure 2:
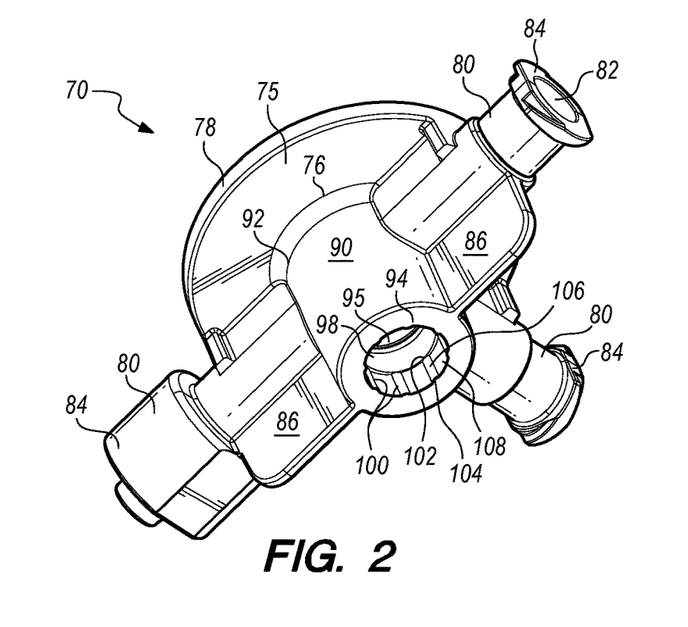
FIG. 2 is a perspective view of a housing of the stopcock of this invention according to the preferred embodiment.
Figure 3:
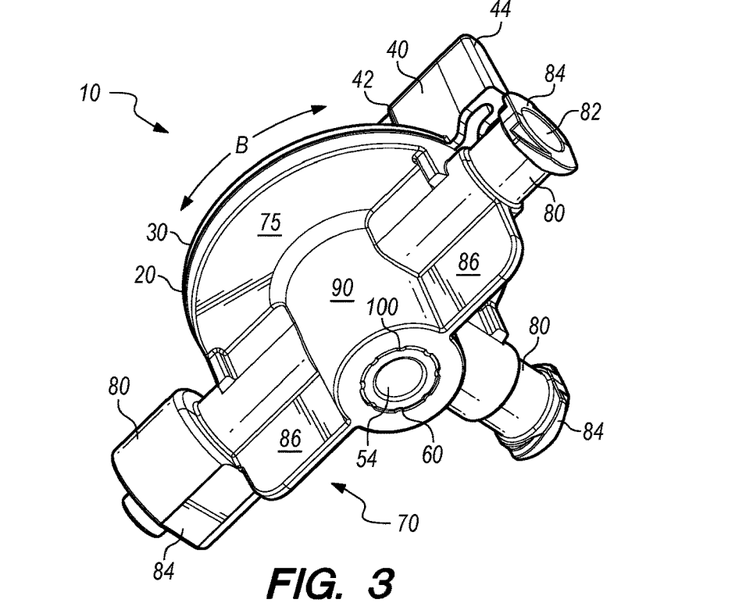
FIG. 3 is a perspective view of the stopcock assembly including the insert of FIG. 1 and the housing of FIG. 2 assembled together according to the first embodiment stopcock of this invention.

In essence, and with particular reference to FIGS. 1-3, basic details of the stopcock 10 are described, according to a preferred embodiment. The insert 20 of the stopcock 10 defines a first structure which rotates relative to the housing 70 defining a second structure of the stopcock 10. The insert 20 includes a top plate 30 in this preferred embodiment which can include flow indicating structures thereon for assistance in communicating with the operator the operational state of the stopcock 10. A knob 40 is preferably provided on the insert 20 which facilitates easy gripping of the insert 20 for rotation (along arrow B of FIG. 3) between different operational states relative to the housing 70. A manifold shaft 50 extends axially along a central axis of the insert 20 away from the top plate 30. Detent slots 60 (or optionally detent ribs) extend radially inwardly into the manifold shaft 50 and cooperate with the detent ribs 100 to tend to keep the stopcock 10 from having any orientations other than precisely defined orientations corresponding with desired operational states (various different ports open or closed, or all ports closed) for the stopcock 10.

Figure 8:
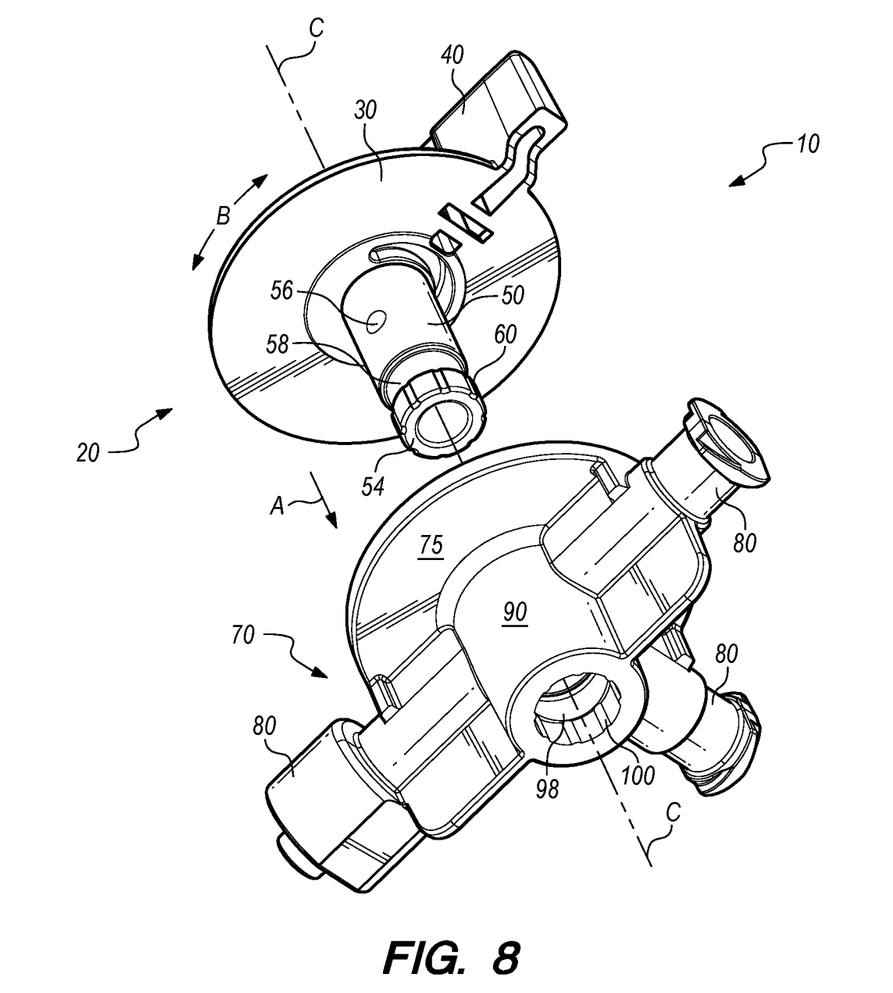
FIG. 8 is a perspective exploded view of that which is shown in FIG. 3, revealing how the insert and the housing are aligned relative to each other.

The housing 70 defines the second structure relative to which the insert 20 is supported and rotates. This housing 70 includes a plurality of ports 80 extending radially from a hub 90 which surrounds a hollow core 95 extending axially and aligned with the central axis C. The manifold shaft 50 of the insert 20 resides within this hollow core 95 of the hub 90 and prevents the insert 20 from any motion relative to the housing 70 other than rotational motion about the central axis C (FIG. 8). Detent ribs 100 extend radially from an inner surface of the hollow core 95. The detent ribs 100 cooperate with the detent slots 60 to cause the stopcock 10 to resist any rotational orientation other than desired operational states for the stopcock 10.

More specifically, and with particular reference to FIG. 1, details of the insert 20 are descried, according to the preferred embodiment of this invention. With regard to the particular details of the insert 20 and housing 70, and the stopcock 10 generally of this preferred embodiment, two configurations thereof are described in detail in U.S. Pat. No. 8,584,701 and U.S. Published Patent Application No. 2015/0129061, each incorporated herein by reference in their entireties.

The insert 20 is preferably formed from a unitary mass of common rigid material, most preferably an injection moldable plastic material which resists chemical or other interaction with fluids which might pass therethrough, and especially liquids. When the stopcock 10 is to be used in a medical setting it is further desirable that the material from which the insert 20 (and housing 70) is formed be biocompatible in that it avoids toxic or other detrimental effects when handling bodily fluids or fluids which are to be introduced into the body of a patient. The insert 20 can be formed by injection molding or through other manufacturing techniques. While the insert 20 is preferably formed as a single unitary mass of material, it could be formed from separate parts which would then be assembled together to provide the completed insert 20.

The insert 20 includes a top plate 30 in a preferred embodiment, which is in the form of an annular planar structure extending from an inner edge 42 to an outer edge 44. The inner edge 42 is located adjacent to the manifold shaft 50 with the outer edge 44 is radially spaced from the manifold shaft 50. The top plate 30 interacts with a base plate 75 of the housing 70 to provide an indication as to the operational state of the stopcock 10. This indication is visually perceptible, so that a user can look at the top plate 30 and base plate 75 interaction together and receive information which can be interpreted to indicate which ports are open or if all of the ports are closed.

In one embodiment, this indication is provided by the top plate 30 and base plate 75 by forming windows in the top plate 30 which pass entirely therethrough so that portions of the base plate 75 can be seen through these windows in the top plate 30. The windows in the top plate 30 would be aligned with openings 56 in the manifold shaft 50. Visually perceptible indicia on the base plate 75 would be aligned with the ports 80 of the housing 70 which indicate an open state for the stopcock 10 and be placed on the base plate 75 out of alignment with the ports 80 which indicate a closed state. Thus, when an operator views the bottom plate 75 through the windows in the top plate 30, the user sees the appropriate operational state indicia indicating which ports 80 are open and which ports 80 are closed, or if all ports 80 are closed (or potentially with all ports 80 open).

Other forms of indicia or arrangements could be utilized between the top plate 30 and base plate 75 to communicate operational state of the stopcock 10. For instance, the top plate 30 could have a lesser diameter at the outer edge 34 than that of the base plate 75, and indicia on the base plate 75 could be provided near a perimeter thereof which can be viewed, and in place of windows in the top plate 30, other markings could be provided which could be brought into or out of alignment with various different indicia on the base plate 75 as the insert 20 rotates relative to the housing 70 and indicate operational state of the stopcock 10.

The knob 40 preferably is a rigid structure extending above the top plate 30 and on a side of the insert 20 opposite the manifold shaft 50. This knob 40 extends from an inner end 42 near the central axis C of the stopcock 10 to an outer end 44 which most preferably extends beyond the outer edge 34 of the top plate 30. The knob 40 can thus be readily gripped by fingers of a user and facilitate application of torque to the insert 20 to cause the insert 20 to rotate relative to the housing 70. Traditionally, the knob 40 has been oriented extending radially relative to the central axis C in a position which is spaced from all of the openings 56 in the manifold shaft 50, so that the position of the knob typically defines an "off" orientation which causes ports adjacent to the knob to be closed. However, the knob 40 could have other orientations if desired.

The manifold shaft 50 extends axially, aligned with the central axis C and perpendicular to a plane in which the top plate 30 is oriented. This manifold shaft 50 extends from a root 52 adjacent to the top plate 30 to a tip 54. The openings 56 in the manifold shaft 50 extend radially away from the central axis where they intersect with an outer surface of the manifold shaft 50. Manifold lines (also referred to as manifold pathways) pass through the manifold shaft 50 to cause the openings 56 to be in fluid communication with each other. In the embodiment depicted (FIG. 3) and with three ports 80 on the housing 70, three openings 56 would be provided on the manifold shaft 50.

In this embodiment, where the three ports 80 are positioned with a 90° spacing between adjacent ports 80, the openings 56 would correspondingly be positioned on the manifold shaft 50 so that 90° of spacing would be provided between adjacent openings 56. With three openings 56, one side of the manifold shaft 50 has no openings thereon and two openings 56 are provided on opposite sides of the manifold shaft 50 and a side of the manifold shaft 50 opposite the side which has no openings has one opening 56 centrally located thereon.

If the ports 80 have a different orientation relative to each other and spacing therebetween of an angular character, the openings 56 of the manifold shaft 50 would be adjusted to match the relative orientation and spacing of the ports 80 in the housing 70. If only two ports 80 are provided on the housing 70, typically only two openings 56 would be provided on the manifold shaft 50 and having a similar orientation to that of the ports 80 relative to each other. If more than three ports 80 are provided on the housing 70, similarly a corresponding number of openings 56 would be provided on the manifold shaft 50 and with the position of the openings 56 again corresponding in angular spacing to the angular spacing of the ports 80 from each other.

While in some embodiments the opening 56 can have a seal circumscribing it at the surface of the manifold shaft 50, preferably the manifold shaft 50 is formed with a tight tolerance relative to the hollow core 95 of the hub 90 (after insertion of the shaft 50 into the core 95 along arrow A of FIG. 8), so that the openings 56 do not need to have seals and still resist leakage. Furthermore, preferably the material from which the insert 20 is formed is at least somewhat hydrophobic so that liquids tend to resist leakage through any small cracks between the hollow core 95 and the manifold shaft 50, adjacent to the openings 56. To further assist in sealing the stopcock 10, a seal trough 58 can be provided if desired which can receive an O-ring or other circular seal therein.

The manifold shaft 50 can optionally have a central bore passing therethrough. This central bore preferably is closed both adjacent to the root 52 and adjacent to the tip 54 of the manifold shaft 50. In an alternative embodiment, the tip 54 of the central bore could be left open to facilitate axial flow along the central axis C and to facilitate fluid flow therethrough. Such axial flow could also conceivably be facilitated through an upper surface of the insert 20 through a center of the top plate 30.

The tip 54 of the manifold shaft 50 (or other position on the manifold shaft 50) preferably includes one-half of a detent system thereon, most preferably in the form of detent slots 60 (or other recesses), but optionally in the form of detent ribs (or other prominences) formed thereon. Such detent structures are of complementary form and position to work together as shown and described. This portion of the detent system is preferably provided adjacent to the tip 54 so that it is sufficiently far from the openings 56 that any distortion associated with interaction of the detent slots 60 with detent ribs 100 does not tend to cause the openings 56 to leak within the hollow core 95 of the hub 90.

The detent slots 60 are elongate in form in this embodiment, extending from an upper end 62 to a lower end 64 which are aligned parallel with the central axis C of the stopcock 10. The detent slots 60 are provided as an arcuate trough 66 extending between the upper end 62 and lower end 64 preferably with a constant cross-sectional form. Intermediate plateaus 68 define space between adjacent detent slots 60, which intermediate plateaus 68 preferably are flat and maintain a constant radial distance away from the central axis C (FIG. 8). The arcuate trough 66 is preferably semi-cylindrical in geometric form, but could have other shapes other than a semi-circular cross-sectional shape.

The detent slots 60 are provided as a set of multiple slots 60 which are located at regular intervals angularly spaced from each other. This spacing is a regular spacing which in one embodiment can match a number of ports and openings so that the slots 60 receive detent ribs 100 only when the openings 56 of the manifold shaft 50 are aligned with the ports 80. However, most preferably additional detent slots 60 (and detent ribs 100) are provided. In particular, and in the embodiment disclosed with three ports each spaced from each other by 90°, eight detent slots 60 are provided. Four of these detent slots correspond with operational states for the stopcock 10 where various different sets of two of the ports 20 are open, or all three ports are open or all three ports are closed.

Furthermore, four other detent slots 60 are provided at intermediate locations which also define closed states for the stopcock 10. Many medical professionals have been trained to operate a stopcock 10 in a manner where they recognize that the stopcock 10 can be closed to all ports merely by placing the insert 20 portion of the stopcock 10 at an intermediate location between various different open orientations and the stopcock 10 transitions to a closed state. With this invention, such intermediate locations are provided with detent slots 60 so that such an intermediate closed state can be precisely provided, rather than only approximated. Furthermore, the standard closed state for all of the spaces is also provided by the detent slots 60, as well as the three different operational open states.

If a stopcock having only two ports spaced angularly 180° from each other were provided, the detent slots could be provided in a set of four and have two open orientations and two closed orientations which would each reliably hold the stopcock. As an alternative, such a two port stopcock could be provided with eight detent slots (and eight detent ribs) similar to that disclosed in this preferred embodiment.

If ports are provided in positions other than 90° away from each other, the detent slots can either be provided in a corresponding angular spacing or with a corresponding angular spacing in addition to provision of detent slots at intermediate locations between each position for each port. Thus, if ports were provided 120° spaced from each other three detent slots could be provided each 120° from each other or six detent slots could be provided each spaced 60° from each other. In such a fashion, the detent slots (and detent ribs) are precisely positioned where desired so that all of the operational states for the stopcock correspond with the detent slots aligned with detent ribs for secure holding of the stopcock in one of these desired operational states.

With particular reference to FIG. 2, details of the housing 70 are described, according to this preferred embodiment. The housing 70 is preferably formed as a rigid unitary mass of material preferably from a common material with that forming the insert 20, but optionally from some alternative material. The housing 70 could be provided as a single unitary mass or from separate structures which are then assembled together to provide this completed housing 70.

The housing 70 includes a base plate 75 in the form of a planar arcuate structure oriented to be positioned parallel with the top plate 30 of the insert 20. This base plate 75 has an inner edge 76 adjacent to the hub 90 and an outer edge 78 spaced from the inner edge 76. Indicia are typically provided on the base plate 75 which cooperate with indicia or windows on the top plate 30 to provide a visual indicia as to the operational state of the stopcock 10. The base plate 75 (and top plate 30) could be dispensed with (see the alternative stopcock 110 of FIGS. 9 and 10) if desired.

The housing 70 includes a plurality of ports 80 extending radially from the central hub 90. These ports 80 define structures which provide inlets or outlets through the stopcock 10 and to which other structures can be readily attached and detached. Pathways 82 within each port 80 extend through to the hollow core 95 of the hub 90 where they come adjacent to one of the openings 56 of the manifold shaft 50 (unless the stopcock 10 is in a closed orientation) to allow fluid flow through the stopcock 10 from ports 80 aligned with these openings 56 in the manifold shaft 50.

Couplings 84 are provided on each port 80 which are typically on an outer surface and/or end of each port 80 and facilitate secure removable attachment of adjacent fluid input or output structures to the stopcock 10. As an alternative, the stopcock 10 could be built into some structure in a permanent or semi-permanent manner, in which case one of these ports 80 would be a permanently affixed port and other ports 80 would have couplings 84 thereon for removable attachment of adjacent fluid handling structures. In this embodiment, gussets 86 are provided adjacent to at least some of these ports 80 to further support these ports 80 and to allow a second hand of a user to grip the housing 70 more readily while a first hand of the user is gripping the knob 40 or other portions of the insert 20 for relative rotation of the insert 20 relative to the housing 70 (along arrow B of FIG. 3).

The hub 90 is oriented along the central axis C and surrounds the hollow core 95. The hub 90 extends from a crown 92 adjacent to the base plate 75 to a base 94. The base 94 is generally preferably adjacent to the tip 54 of the manifold shaft 50 which is contained within the hollow core 95 of the hub 90. A seal groove 98 can optionally be circumscribed within an interior of the hollow core 95 preferably slightly up from the base 94 to facilitate holding of an O-ring or other seal structure if desired. This space could alternatively be utilized to support a bearing structure to facilitate rotation of the insert 20 relative to the housing 70.

Adjacent to the base 94 of the hub 90 and within the hollow core 95, the detent ribs 100 (or other detent prominences) extend radially inwardly. These detent ribs 100 are generally positioned to come into and out of alignment with the detent slots 60 (or other detent recesses) of the manifold shaft 50 (described in detail above). Each detent rib 100 preferably extends from a top end 102 to a bottom end 104 with this extension being generally linear and parallel with the central axis C (FIG. 8) of the stopcock 10. Each detent rib 100 preferably has a curving surface 106 when viewed in cross-section perpendicular to the central axis C, so that the curving surface 106 generally has a semi-cylindrical form. Other forms for this surface 106 of the detent ribs 100 could alternatively be provided, and preferably matches a geometry of the detent ribs 60. Intermediate flats 108 are preferably provided between adjacent detent ribs 100 which are generally arcuate and maintain a constant distance away from the central axis C (FIG. 8).

As described above, while detent ribs 100 are shown extending radially inwardly from the hollow core 95 of the hub 90, alternatively detent slots 60 (or other recesses) could be provided on the inner surface of the hollow core 95 rather than the detent ribs (or other prominences). The detent ribs 100 are provided in a common number with that of the detent slots 60 and have a spacing relative to each other which is similar to a spacing between adjacent detent slots 60. The sizing of the detent ribs 100 is preferably the same as that of the detent slots 60 so that a tight fit is provided between the detent ribs 100 and detent slots 60. Some amount of tolerance could be provided (or an interference fit) following design criteria to maximize the desirable and convenient holding of the stopcock 10 with ribs 100 located within slots 60, rather than misalignment with the ribs 100 outside of the slots 60. Most desirably, the stopcock 10 has a performance which tends to "snap" into a desired operational state with the ribs 100 snapping into the slots 60 when so desirably oriented.

Figure 9:
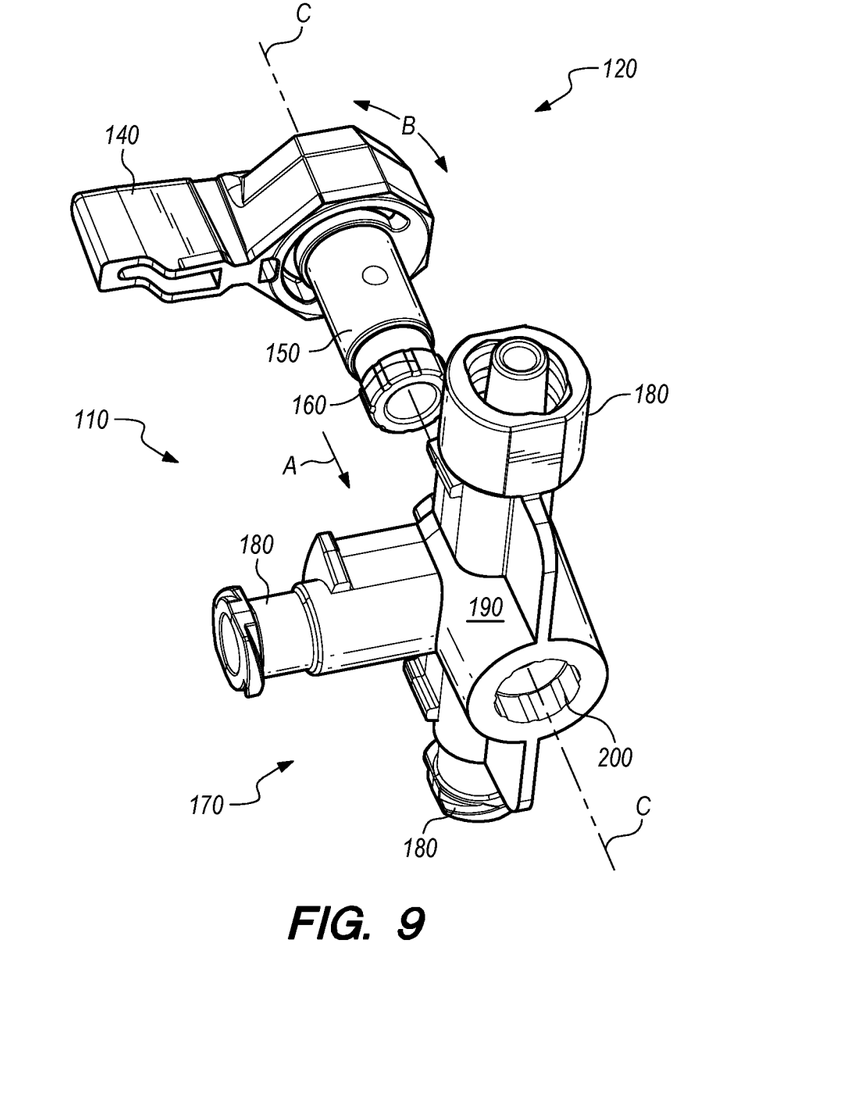
FIG. 9 is an exploded parts view of an alternative embodiment of that which is shown in FIG. 8 without indicator plates.
Figure 10:
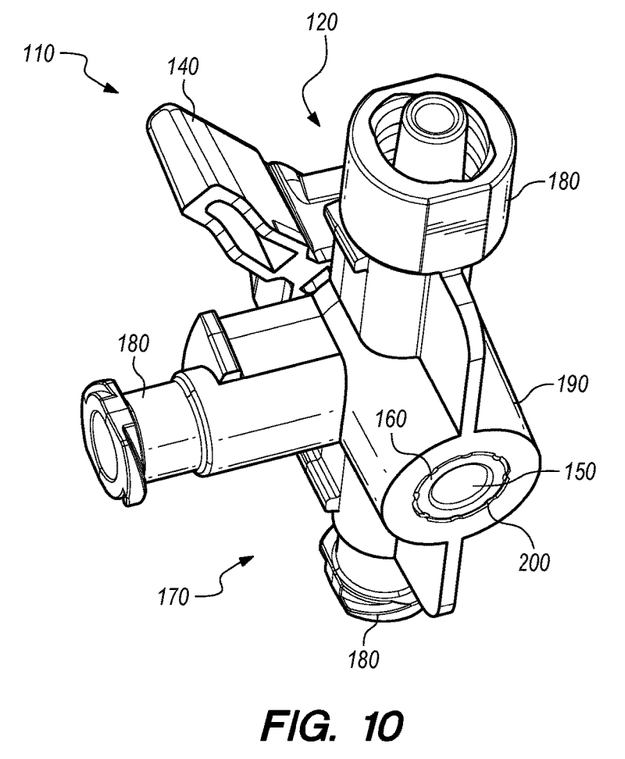
FIG. 10 is a perspective view of the alternative embodiment of FIG. 9 in an assembled configuration, corresponding with the assembled configuration of FIG. 3 for the preferred embodiment.

With particular reference to FIGS. 9 and 10, details of an alternative stopcock 110 are described. This alternative stopcock 110 is similar to the stopcock 10 of the preferred embodiment except that the top plate 30 and base plate 75 are not provided. This alternative stopcock 110 illustrates how the stopcock of this invention can be provided with or without the top plate 30 and base plate 75 and still provide the reliable operation goals of this invention. The alternative stopcock 110 thus includes an insert 120 and a housing 170 which rotate relative to each other. The insert 120 includes a knob 140 and a manifold shaft 150, as well as detent slots 160 (or other recesses). The housing 170 includes ports 180 and a hub 190, as well as detent ribs 200 (or other recesses) which generally correspond with similar structures in the stopcock 10 (FIGS. 1-8). The insert 20 is initially placed within the housing 70 by translation (along arrow A of FIG. 9) and along the central axis C, with the detent ribs 100 being deflected somewhat as this axial translation occurs until the insert 20 is fully positioned with its manifold shaft 50 residing within the hollow core 95 and the detent slots 60 and detent ribs 100 aligned together, so that the insert 20 is held securely within the housing 70. If desired, an O-ring can first be placed within the seal trough 58 on the manifold shaft 50, before this axial positioning of the insert 20 within the housing 70.

In use and operation and with reference to FIGS. 3-7, the stopcock 10 assembly can be seen in five different orientations, rotated various amounts along arrow B and indicated by the position of the knob 40 in each of the sequential figures. In FIG. 3, if the manifold lines are arranged relative to the knob 40 with the knob at a 9 o'clock position and with the manifold line openings 56 at the 12 o'clock, 3 o'clock and 6 o'clock positions, FIG. 3 would depict a position for the stopcock 10 where the two lower ports 80 would be open and the port 80 adjacent to the knob 40 would be closed. Note that each of the detent ribs 100 is located within a detent slot 60 so that the stopcock 10 provides strong confirmation to a user that the stopcock 10 is properly and securely positioned in this orientation. The two indicator plates 30, 75 would coact in a manner which would provide visual confirmation to the user as to which of the two ports 80 are open.

Figure 4:
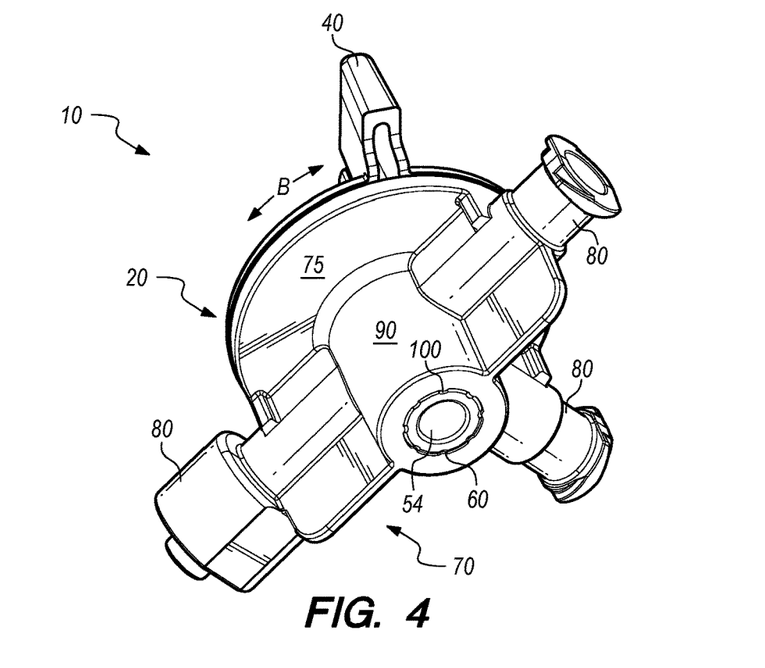
FIGS. 4-7 are perspective views similar to that which is shown in FIG. 3, but with the insert of the stopcock placed in various different rotational orientations relative to the housing.

In FIG. 4, the knob 40 has been rotated 45° and the detent ribs 100 and slots 60 are again aligned. However, in this position the openings 56 at the tips of the manifold lines are out of alignment with the fluid pathways extending from the ports 80 in the housing 70. Thus, each of the ports 80 is closed in this orientation. The indicator plates 30, 75 would either provide a positive indication as to the closed state of each of the ports 80 or provide lack of confirmation that any of the ports 80 are opened, which can be similarly inferred to as the stopcock 10 being in a closed orientation. The detents 60, 100 hold the stopcock 10 in this fully closed orientation, giving the user confidence that the stopcock 10 has been appropriately rotated to turn off all of the ports 80, by having the insert 20 snap securely into this closed orientation shown in FIG. 4.

Figure 5:
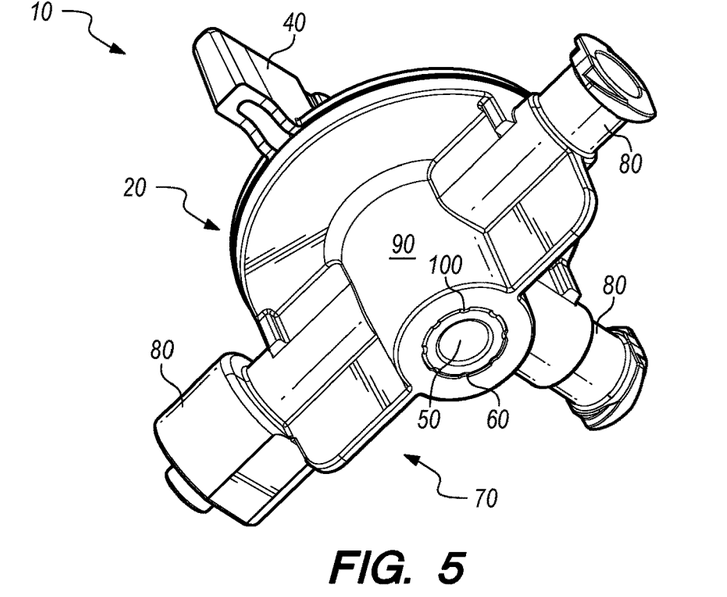
Figure 6:
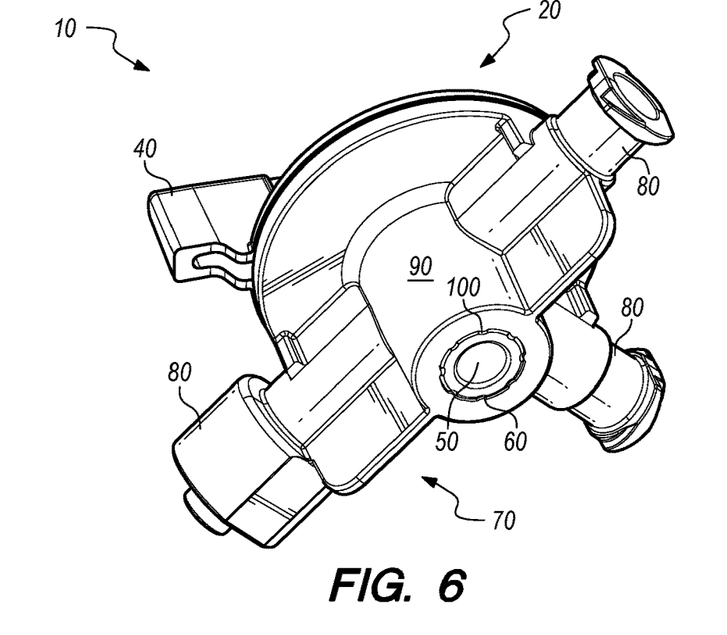

With reference to FIG. 5, further rotation of the knob 40 along arrow B to the next position corresponds with a position where each of the ports 80 align with each of the openings 56 in the manifold line so that each of the ports 80 is open. The detent ribs 100 and slots 60 are again aligned to securely hold the stopcock 10 in this fully open position. The indicator plates 30, 75 would similarly be aligned to provide clear confirmation to the operator that all of the lines are open. In FIG. 6, the knob 40 has been further rotated another 45° to a position where each of the ports 80 are again closed, similar to that described above with reference to FIG. 4.

Figure 7:
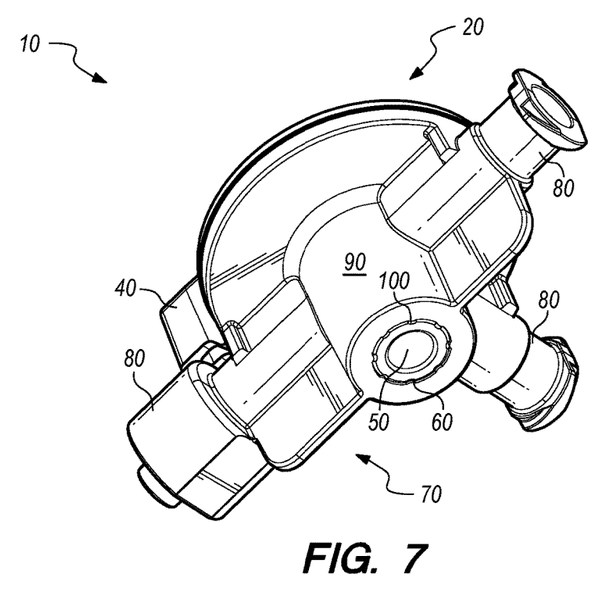

In FIG. 7, the knob 40 has been further rotated so that now two other ports spaced from the knob 40 are open and the port 80 adjacent to the knob 40 is closed. The detent ribs 100 and slots 60 are again aligned to securely hold the stopcock 10 in this new position with two of the ports 80 open and one of the ports 80 closed. The indicator plates 30, 75 would provide confirmation to the user as to which ports 80 are open and the detents 60, 100 would provide confidence to the user that the stopcock 10 has been positioned properly in that the stopcock 10 snaps into position when so appropriately aligned.

Furthermore, in each of these positions depicted in FIGS. 3-7, inadvertent bumping of the stopcock 10 is insufficient to cause the insert 20 to rotate relative to the housing 70 in that the ribs 100 and slots 60 are securely aligned together and a greater amount of force is required before they can be dislodged from each other. Hence, only intentional forces applied to the stopcock 10 assembly are capable of reorienting the stopcock 10.

Further rotation of the knob 40 could also occur in additional 45° increments to cause the stopcock 10 assembly to be in two other fully closed positions or in a partially open position where two ports 80 directly opposite each other can be open while a third port intermediate therebetween can be closed, as can be readily discerned through a study of FIGS. 3-7 and logical extrapolation therefrom.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A stopcock comprising in combination:
  a housing having a plurality of ports extending radially from a central hub and with fluid pathways extending through each port into a hollow core of said hub;
  an insert including a manifold shaft sized to fit within said core of said hub, said manifold shaft located within said core of said hub;
  said manifold shaft including at least one manifold line therein which extends between openings on a surface of said manifold shaft;
  said insert adapted to rotate relative to said housing to cause various different ones of said openings of said at least one manifold line to come into and out of alignment with said fluid pathways extending through said ports, such that said stopcock can have a variety of different operational states with various different ones of said ports open or closed to fluid flow in different operational states;

said manifold shaft extending from a root to a tip along a central axis;

a plurality of detent prominences, each of said detent prominences extending radially relative to said central axis;

a plurality of detent recesses, each of said detent recesses extending radially relative to said central axis;

said detent prominences and said detent recesses defining detent structures which fit together, at least one of said detent structures extending radially from said manifold shaft and at least one of said detent structures extending radially from said core of said hub;

said detent recesses selectively alignable with said detent prominences at a plurality of different relative orientations between said insert and said housing, at least one of said relative orientations corresponding with one of said variety of different operational states of said stopcock;

wherein said detent prominences extend radially outwardly from said manifold shaft and said detent recesses extend radially into an inner surface of said core of said hub;

wherein said detent prominences extend radially inwardly from said inner surface of said core of said hub and said detent recesses extend radially into said manifold shaft;

wherein plateaus are provided between said detent recesses, said plateaus being flat to maintain a substantially constant radial distance from said central axis;

wherein said housing includes at least three ports spaced about 90° from at least one adjacent said port about said central axis of said stopcock; and wherein said prominences and said recesses have an angular spacing circumferentially away from adjacent prominences and recesses equal to about 45°.

2. The stopcock of claim 1 wherein said prominences and said recesses are located closer to said base of said hub and said tip of said manifold shaft than to said crown of said hub and said root of said manifold shaft.

3. The stopcock of claim 1 wherein said prominences are in the form of ribs with an elongate form oriented substantially parallel with said central axis of said stopcock and said recesses are in the form of elongate slots sized similarly to said ribs and extending substantially parallel with said central axis of said stopcock.

4. A stopcock comprising in combination:

a housing having a plurality of ports extending radially from a central hub and with fluid pathways extending through each port into a hollow core of said hub;

an insert including a manifold shaft sized to fit within said core of said hub, said manifold shaft located within said core of said hub;

said manifold shaft including at least one manifold line therein which extends between openings on a surface of said manifold shaft;

said insert adapted to rotate relative to said housing to cause various different ones of said openings of said at least one manifold line to come into and out of alignment with said fluid pathways extending through said ports, such that said stopcock can have a variety of different operational states with various different ones of said ports open or closed to fluid flow in different operational states;

said manifold shaft extending from a root to a tip along a central axis;

a plurality of detent prominences, each of said detent prominences extending radially relative to said central axis;

a plurality of detent recesses, each of said detent recesses extending radially relative to said central axis;

said detent prominences and said detent recesses defining detent structures which fit together, at least one of said detent structures extending radially from said manifold shaft and at least one of said detent structures extending radially from said core of said hub;

said detent recesses selectively alignable with said detent prominences at a plurality of different relative orientations between said insert and said housing, at least one of said relative orientations corresponding with one of said variety of different operational states of said stopcock;

wherein said detent prominences extend radially outwardly from said manifold shaft and said detent recesses extend radially into an inner surface of said core of said hub;

wherein said detent prominences extend radially inwardly from said inner surface of said core of said hub and said detent recesses extend radially into said manifold shaft;

wherein plateaus are provided between said detent recesses, said plateaus being flat to maintain a substantially constant radial distance from said central axis;

wherein said housing includes at least three ports spaced about 90° from at least one adjacent said port about said central axis of said stopcock; and wherein said prominences and said recesses have an angular spacing circumferentially from adjacent prominences and recesses similar to said spacing between said at least three ports.

5. A stopcock for control of flow between one or more inputs and one or more outputs, the stopcock comprising in combination:

a housing having a plurality of ports extending radially from a central hub aligned with a central axis;

a hollow core extending along said central axis of said housing, and with said plurality of ports accessing said hollow core;

an insert including a manifold shaft located within said core of said hub, said manifold shaft aligned with said central axis of said housing;

said manifold shaft including at least one manifold line passing therethrough, with said at least one manifold line extending between openings at a surface of said manifold shaft;

said insert rotatable relative to said housing about said central axis to cause various different ones of said openings of said at least one manifold line to come into and out of alignment with said ports of said housing, such that said stopcock can have a variety of different operational states with various different ones of said ports opened or closed;

a plurality of prominences extending radially relative to said central axis;

a plurality of recesses extending radially relative to said central axis;

said prominences extending from one of said manifold shaft or said inner surface of said core of said hub, and said recesses located upon the other of said manifold shaft and said core of said hub which does not have said prominences thereon, said prominences and said recesses located in positions on said manifold shaft and said inner surface of said core of said hub which cause said prominences to move into and out of said recesses as said insert rotates relative to said housing;

wherein each of said ports and each of said openings of said manifold lines has at least one of said prominences or at least one of said recesses aligned therewith so that when said openings of said at least one manifold line are aligned with at least one of said ports when at least one of said prominences is located within at least one of said recesses; and wherein said ports are spaced from each other circumferentially an angular distance similar to twice an angular spacing between adjacent said prominences and adjacent said recesses, such that said prominences reside within said recesses both when said ports are aligned with said openings of said at least one manifold line and when said openings of said at least one manifold line are halfway between adjacent said ports.

6. The stopcock of claim 5 wherein said hub extends from a crown to a base, with said base further from said ports than said base, said prominences and said recesses located closer to said base of said hub of said housing than to said crown of said housing.

7. The stopcock of claim 5 wherein said prominences are in the form of ribs with an elongate form oriented substantially parallel with said central axis of said stopcock and said recesses are in the form of elongate slots sized similarly to said ribs and extending substantially parallel with said central axis of said stopcock.

8. A stopcock for control of flow between one or more inputs and one or more outputs, the stopcock comprising in combination:
   a housing having a plurality of ports extending radially from a central hub aligned with a central axis;
   a hollow core extending along said central axis of said housing, and with said plurality of ports accessing said hollow core;
   an insert including a manifold shaft located within said core of said hub, said manifold shaft aligned with said central axis of said housing;
   said manifold shaft including at least one manifold line passing therethrough, with said at least one manifold line extending between openings at a surface of said manifold shaft;
   said insert rotatable relative to said housing about said central axis to cause various different ones of said openings of said at least one manifold line to come into and out of alignment with said ports of said housing, such that said stopcock can have a variety of different operational states with various different ones of said ports opened or closed;
   a plurality of prominences extending radially relative to said central axis;
   a plurality of recesses extending radially relative to said central axis;
   said prominences extending from one of said manifold shaft or said inner surface of said core of said hub, and said recesses located upon the other of said manifold shaft and said core of said hub which does not have said prominences thereon, said prominences and said recesses located in positions on said manifold shaft and said inner surface of said core of said hub which cause said prominences to move into and out of said recesses as said insert rotates relative to said housing;
   wherein each of said ports and each of said openings of said manifold lines has at least one of said prominences or at least one of said recesses aligned therewith so that when said openings of said at least one manifold line are aligned with at least one of said ports when at least one of said prominences is located within at least one of said recesses; and
   wherein said ports are spaced circumferentially from each other an angular distance similar to a spacing between adjacent ones of said prominences and said recesses.

9. A method for controlling fluid flow through a stopcock, the method including the steps of:
   manually grasping an insert of a stopcock and rotating the insert relative to a housing of the stopcock, the housing having a plurality of ports extending radially from a central hub having a hollow core aligned with a central axis, and the insert including a manifold shaft located within the core of the hub, the manifold shaft aligned with the central axis of the housing, the manifold shaft including at least one manifold line therein extending between openings at a surface of the manifold shaft, the insert rotatable relative to the housing to cause various different ones of the openings of the at least one manifold line to come into and out of alignment with the ports such that the stopcock can have a variety of different operational states with the various different ones of the ports open or closed in different ones of the operational states;
   said rotating step including moving prominences between recesses, the prominences extending radially relative to the central axis and the recesses extending radially relative to the central axis with the prominences sized to fit within the recesses and with one of either the prominences or the recesses associated with the manifold shaft and the other of the plurality of prominences and recesses associated with the core of the hub;
   stopping the rotating step with the insert oriented relative to the housing with the plurality of prominences residing within the plurality of recesses;
   wherein the number of prominences and recesses is twice as great as the number of ports, such that the prominences reside within the recesses in some relative orientations where the ports are aligned with the openings in the at least one manifold line and other orientations where the ports are out of alignment with the openings in the manifold lines to define a closed operational state.

10. The method of claim 9 wherein said manually gripping the insert step includes manually gripping a knob on a side of the insert opposite the manifold shaft.

* * * * *